United States Patent
Andersen et al.

(10) Patent No.: US 7,125,516 B2
(45) Date of Patent: Oct. 24, 2006

(54) VACUUM DRYING PROCESS USED FOR MANUFACTURING DIALYZER

(75) Inventors: Marion Andersen, Kaysville, UT (US); Marvin Lyon, North Ogdan, UT (US); G. Neivell Allan, Ogden, UT (US); Wade Paskett, Roy, UT (US)

(73) Assignee: Fresenius USA, Inc., Lexington, MA (US)

( * ) Notice: Subject to any disclaimer, the term of this patent is extended or adjusted under 35 U.S.C. 154(b) by 58 days.

(21) Appl. No.: 10/421,602

(22) Filed: Apr. 23, 2003

(65) Prior Publication Data

US 2004/0213697 A1  Oct. 28, 2004

(51) Int. Cl.
*A61I 2/07* (2006.01)

(52) U.S. Cl. ............... 422/26; 34/381; 34/404; 34/411; 34/427; 210/636; 210/321.69

(58) Field of Classification Search ............ 422/26; 34/381, 403, 404, 411, 427; 210/636, 646, 210/764, 321.69
See application file for complete search history.

(56) References Cited

U.S. PATENT DOCUMENTS

| | | | | |
|---|---|---|---|---|
| 4,411,866 | A | * | 10/1983 | Kanno ............... 422/25 |
| 4,657,540 | A |   | 4/1987  | Iwamoto et al. |
| 4,687,635 | A | * | 8/1987  | Kaehler et al. ...... 422/26 |
| 4,759,909 | A | * | 7/1988  | Joslyn ............... 422/26 |
| 4,810,469 | A | * | 3/1989  | Masuhara ........... 422/26 |
| 5,147,613 | A | * | 9/1992  | Heilmann et al. ..... 422/116 |
| 5,429,800 | A | * | 7/1995  | Miraldi et al. ...... 422/26 |
| 5,891,340 | A | * | 4/1999  | Akiyama et al. ..... 210/636 |

FOREIGN PATENT DOCUMENTS

WO   WO 200176646 A1 * 10/2001

OTHER PUBLICATIONS

University of Cincinnati, Regulations for Autoclave Use, Maintenance and Recordkeeping, http://ehs.uc.edu/Advisories/Advisory_10_5.PDF, prior art.
Procedures for Disposal of Hazardous Waste, Chapter Three—Biological Waste, http://www.utexas.edu/safety/ehs/disposal/haswaste/chap3.html, prior art.
ITG Subject: Steam Pressure Control for Retorts and Autoclaves, Jun. 29, 1973, http://www.fda.gov/ora/inspect_ref/itg/itg11.html.
Treatment Manual, Nonchemical Treatments, http://www.aphis.usda.gov/ppq/manuals/pdf_files/Treatment%20Chapters/03-04-NonChemHeatStream.pdf, prior art.
AMSCO, Eagle® 3000 Equipment Manual, vol. 1. Service and Maintenance Procedures, prior art.
Nam Sun Wang, Experiment No. 8A, Aseptic Culture Techniques, Use of a Steam Autoclave, http://www.glue.umd.edu/~nsw/ench485/lab8ahtm, prior art.
Autoclave Safety Manual, University of Nevada, Reno, http://www.ehs.unr.edu/Portals/0/Autoclave.pdf, prior art.

* cited by examiner

*Primary Examiner*—E. Leigh McKane
(74) *Attorney, Agent, or Firm*—Fish & Richardson P.C.

(57) ABSTRACT

A method of sterilizing and drying a dialyzer or other device, wherein a vacuum drying phase is interrupted by interspersed pulses of air or other gas. The pulses lessen the evaporative cooling effect, to thereby reduce differential shrinkage that can structurally damage the dialyzer.

24 Claims, 2 Drawing Sheets

VACUUM DRYING PROCESS USED FOR MANUFACTURING DIALYZER

FIELD OF THE INVENTION

This invention relates to the field of dialyzers typically used in hemodialysis and related medical procedures, and in particular to a process for manufacturing a dialyzer with a strong and integral bond between a potting material holding dialysis fibers and a dialyzer housing.

BACKGROUND OF THE INVENTION

Patients with kidney disease suffer from the adverse effects of toxin build-up in their blood. Dialysis is a process which employs an artificial kidney to remove those toxins. In hemodialysis a dialyzer is used which contains a semipermeable membrane dividing the dialyzer into two chambers. Blood is pumped through one chamber and a dialysis solution through the second. As the blood flows by the dialysis fluid, separated by the semipermeable membrane, blood impurities such as urea and creatinine diffuse through the semi-permeable membrane into the dialysis solution by the diffusion, convection and absorption. The electrolyte concentration of the dialysis fluid is set so as to maintain electrolytic balance within the patient.

The semi-permeable membrane is often a large number of microfibers encased in a chamber. The chamber is often a hollow cylinder open at both ends. Thousands of hollow semipermeable microfibers carry blood from one end to the opposite end so that blood flows through the microfibers in a first direction. Dialysate ports are also present on opposite ends of the chamber. One port carries dialysate into the chamber, the dialysate flows through the chamber in a countercurrent direction to the blood flow, and the other port carries the dialysate out of the chamber. The solute removal thus takes place across the semipermeable membrane that is the microfiber wall. This design produces a high surface area for solute removal in a relatively low volume device.

One significant challenge is to connect the microfiber interior channels to the blood lines, so that blood flows smoothly from the arterial blood line, into the microfiber interior channels where it can pass into and through the dialyzer chamber, and out the other end of the microfiber interior channels to the venous blood line.

This is done by potting the microfiber ends with a potting material. The potting material encases the microfiber ends to seal them from the chamber interior and to hold them in position within the chamber. The end result is a dialyzer in a generally cylindrical shape with a hollow interior chamber. Ports at each end of the chamber allow passage of dialysate therethrough. Within the chamber are the microfibers, positioned longitudinally so that their ends extend to the respective chamber ends. The blood passes through the lumens of the microfibers in the opposite direction from the direction of dialysate movement through the dialyzer chamber. The blood is thus separated from the dialyzer by the microfiber walls. At each end of the chamber, the microfiber lumens are open to the exterior of the dialyzer, which is fitted with the blood lines to carry blood between the dialyzer and the patient. The microfibers are held in place, and the dialyzer chamber is sealed from its ends, by the potting material.

This potting material is typically epoxy or urethane. It is injected into the dialysate ports on each end of the chamber, and the dialyzer is spun in a centrifuge. The centripetal force produced by the rotation in the centrifuge forces the potting material to each end, where it sets and hardens.

One of the manufacturing steps for a dialyzer, like many other medical devices that come into contact with body fluid, is sterilization. It is important that the dialyzer be free of pathogens that could migrate into the blood flowing through the microfiber lumens and thereby enter the patient's bloodstream.

A common method of sterilizing medical devices is by heated steam in an autoclave. Hot steam is introduced to kill pathogens to an acceptable level, and then the steam is removed and the device is allowed to cool. The removal of the steam is facilitated by a vacuum drying cycle; a vacuum is applied which draws off the remaining steam and any condensate.

It has been discovered that steam autoclaving as a method for sterilizing a dialyzer can affect the structural integrity of the dialyzer. Specifically, dialyzers subjected to steam autoclaving often show delamination between the potting material used to pot the microfibers in place and the dialyzer housing. The result may be a gap between the potting material or at least a structural discontinuity.

Investigation reveals that the reason for this delamination effect upon steam autoclaving may be two-fold. First, the potting material and the dialyzer housing typically have different coefficients of thermal expansion because they are made of different types of materials. The potting material is commonly a polyurethane, while the dialyzer housing is commonly a polycarbonate. The decrease in temperature at the end of autoclaving produces differential shrinkage between the two materials. This differential shrinkage produces strain at the interface between the materials which, at least in some cases, causes delamination or structural discontinuities.

Second, investigation suggests that the rate of cooling is different in the potting as compared to the dialyzer housing. This appears to be a result of evaporative cooling in the potting material. Autoclave steam condenses or collects to some extent on the surfaces of the dialyzer. Condensate not only collects but also is absorbed into the absorptive microfibers. Upon application of the drying vacuum, the condensate evaporates at different rates from the absorptive material of the microfibers compared to the nonabsorptive materials. The condensate evaporates fastest from the nonabsorptive material, since all the condensate is at the surface and can freely vaporize into the partial vacuum. In comparison, the condensate evaporates into the partial vacuum slower from the absorptive material of the microfibers, because some of the condensate must migrate from the interior of the material to the exterior surface where the molecules can evaporate.

Because the condensate evaporates slowest from the absorptive microfibers, and perhaps because the absorptive microfibers hold a relatively large amount of condensate, they stay moist the longest. At a point in the vacuum drying process, the nonabsorptive surfaces will be essentially dry while the absorptive microfibers are still moist. Continued application of the vacuum drying process beyond this point is necessary to dry the microfibers. At this stage, there is little or no evaporative cooling effect on the dry nonabsorptive surfaces, but there continues to be an evaporative cooling effect on the absorptive microfibers.

This differential evaporation produces differential cooling between the absorptive microfibers and the nonabsorptive materials. Early in the vacuum drying, when there is still condensate on the nonabsorptive materials, they experience relatively large rates of evaporation and consequently relatively rapid cooling. However, this cooling, while rapid, is very short-lived because the nonabsorptive materials have very little condensate on them to begin with. Later in the vacuum drying process, after the nonabsorptive material is essentially dry, the nonabsorptive material experiences relatively no evaporation and consequently relatively slow cooling.

In a typical scenario, the temperature gradients are as follows. The temperature of the entire dialyzer is high and uniform at the conclusion of the steam autoclaving. Upon application of the vacuum dryer process, the temperature of the nonabsorptive materials initially falls quickly to a temperature less than that of the absorptive microfiber due to rapid evaporation from those materials. Once the condensate is fully evaporated from the nonabsorptive materials, however, the temperature of the nonabsorptive materials stabilizes. Continued evaporation from the absorptive materials continues to cool them, so that their temperature becomes as low as the temperature of the nonabsorptive materials, and then even lower.

These temperature gradients due to differential evaporative cooling are mitigated slightly but not fully by other cooling mechanisms. For example, both the nonabsorptive materials and the absorptive materials cool by radiation. They also cool by conduction; that is, the surfaces lose heat to colliding molecules that pass by. This conductive cooling is of little effect, however, since it operates in a high vacuum; there simply are too few passing molecules.

The temperature difference in the absorptive microfibers, as described above, is reflected as well in the potting material into which they are potted. In other words, due to heat conduction through the potting material and the microfibers, the potting material tends to be warmer than the other nonabsorptive materials early in the vacuum drying. Later in the vacuum drying, the potting material tends to be cooler than the other nonabsorptive materials. This appears to be a significant reason for the differential cooling—and resulting differential shrinkage—between the dialyzer housing and the potting material during vacuum drying.

SUMMARY OF THE INVENTION

The present invention addresses the differential shrinkage between the dialyzer housing and the potting material. Rather than applying a continuous vacuum during the vacuum drying phase, the vacuum is interspersed with air or other gas at an atmospheric pressure. This has the effect of reducing the temperature differential between the dialyzer and the potting material in two ways. First, the air at atmospheric pressure has a much greater density of air molecules than are in the vacuum. These molecules produce conductive cooling in the nonabsorptive material of the dialyzer housing, thereby lessening the temperature differential between the dialyzer housing and the potting material.

Second, the atmospheric pressure lessens the evaporation from the microfibers, since a liquid evaporates into a higher pressure gas slower than it evaporates into a lower pressure gas. This interspersed atmospheric pressure thus reduces the rate of evaporation—and consequent evaporative cooling—from the microfibers at the same time that it increases the cooling of the dialyzer housing.

The reduced cooling rate in the microfibers produces a reduced cooling rate in the potting material into which their ends are embedded. The overall effect is a reduction in the temperature differential between the potting material and the dialyzer, so as to lessen the differential shrinkage.

DETAILED DESCRIPTION OF THE INVENTION

Figure 1:
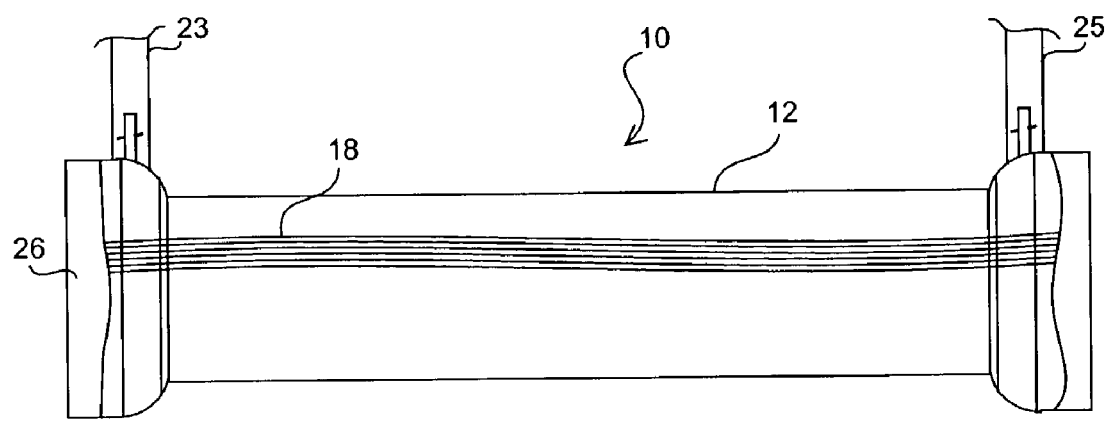
FIG. 1 shows a schematic representation of a dialyzer in accordance with the present invention.

A preferred embodiment of a dialyzer 10 in accordance with the present invention is shown in FIG. 1. The dialyzer 10 includes a housing 12, preferably having a generally cylindrical shape with a hollow interior which defines a dialysate chamber. The ends of the housing 12 have dialysate ports 23 and 25 in fluid communication with the chamber, so that dialysate can flow from one port 23, into the interior chamber of the housing 12, through the chamber, and out the other port 25.

Extending longitudinally within the chamber of the housing are a set of microfibers 18. The microfibers are held in place at their opposite ends by potting material 26 and 28. The potting material is preferably polyurethane or epoxy. It is installed by injecting it in liquid form into the chamber through one or both dialysate ports, 23 and 25, and then centrifuging the dialyzer 10 about an axis perpendicular to its longitudinal axis. The centripetal force produced by the centrifuge pushes the liquid potting material to the opposite ends of the chamber, where itf sets and hardens in the general configuration shown as 26 and 28. The outcome of this procedure is a dialyzer 10 in which the microfiber lumens are completely isolated from the chamber, except via passage through the semipermeable membrane of the microfiber walls.

In a preferred embodiment, the dialyzer housing is constructed of a durable molded material such as a polycarbonate. In particular, polycarbonate is a suitable material. The potting material is a polyurethane or an epoxy. Many other materials are feasible.

The ends of the dialyzer 10 are then cut or sawn off through the potting material 26 and 28 in order to expose the microfiber lumens to the exterior. Fittings (not shown) attach to each end of the dialyzer ends which connect to the blood lines, namely the venous line and arterial line (not shown). Fluid communication is thus established from an arterial line proximate the dialyzer outlet port 25, into the microfiber lumens, through the microfiber lumens within the dialyzer chamber, out of the dialyzer 10 and into a venous line proximate the dialyzer inlet port 23. This general design of dialyzers and method for manufacturing them is known in the art and is not further described here.

In operation, blood flows from a patient into the arterial line and then into the microfiber lumens at the dialyzer 10 proximate the dialysate outlet 25. The blood then flows through the microfiber lumens and out the other end of the dialyzer 10 into a venous line, and back to the patient. Simultaneously, dialysate flows into the dialyzer chamber from the dialysate inlet port 23, through the chamber in the direction opposite the direction of blood flow through the microfiber lumens, and out through the dialysate outlet port 25.

As the blood flows in one direction through the microfiber lumens and the dialysate flows in the opposite direction in the chamber, blood impurities pass from the blood in the microfiber lumens to the dialysate by migrating through the semi-permeable membrane that is the microfiber wall. At the same time, desirable nutrients, drugs or other substances added to the dialysate will pass from the dialysate into the blood, also through the semipermeable membrane that is the microfiber wall. Appropriate dialysis treatment is accomplished by varying the duration of the treatment, the fluid flow, and the make-up of the dialysate in such a system, all in a manner generally familiar to those skilled in the field.

After the dialyzer 10 is manufactured and before it is used, it is sterilized in a steam autoclave device. Such a device ordinarily includes a sterilization chamber in which both the nature of the chamber gas, and its pressure, are controllable. The sterilization medium is usually steam. The steam is initially introduced in pulses in order to remove entrapped air from the dialyzer, and then the steam is allowed to reside in the chamber for a dwell time to destroy any remaining pathogens.

Figure 2:
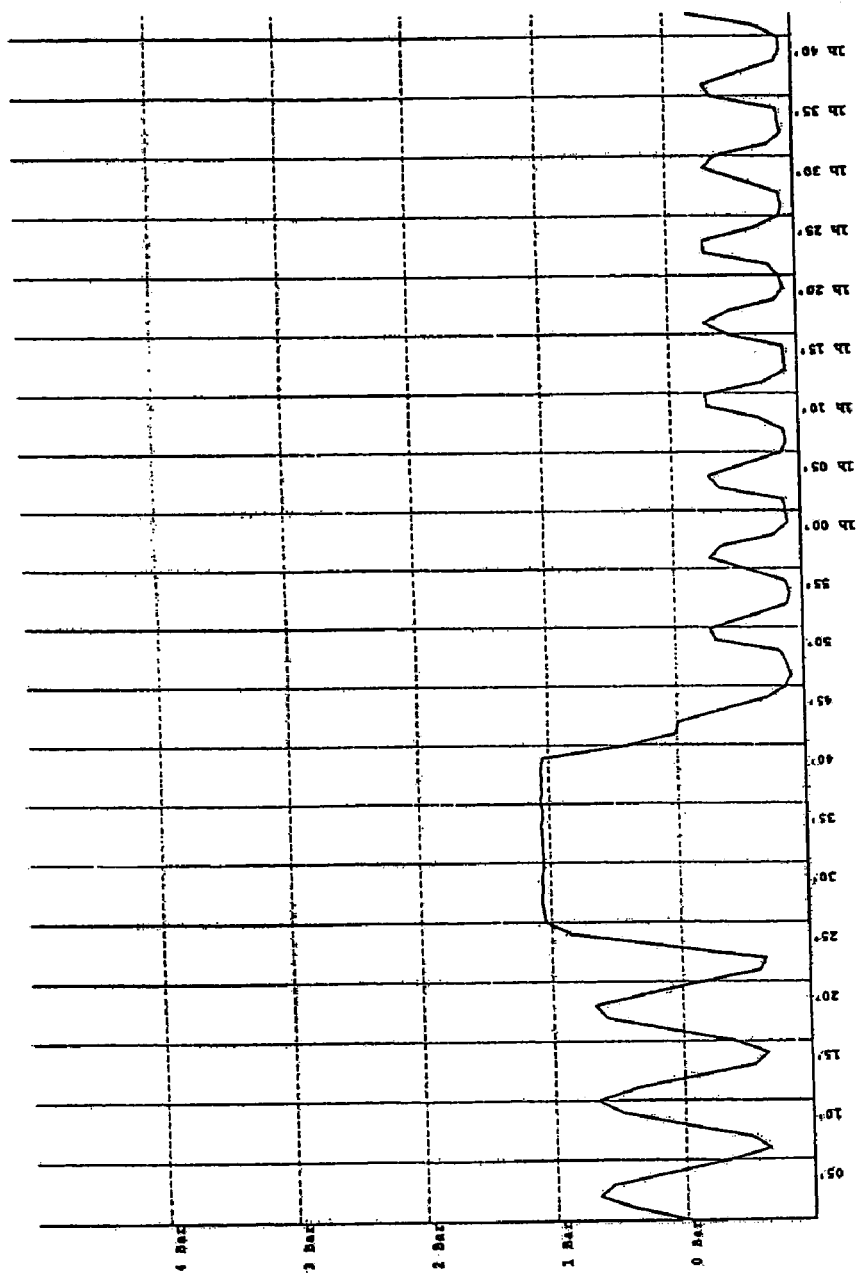
FIG. 2 shows a graph of pressure in a vacuum dryer as a function of time in accordance with a preferred embodiment of the invention.

The steaming process is shown in the graph of FIG. 2, which depicts the chamber steam pressure as a function of time. It can be seen that the chamber pressure is initially at 0 bar, i.e., atmospheric pressure. An initial set of three steam pulses is then applied to remove the entrapped air. In each pulse, the steam pressure rises to approximately positive 0.7 bar, then is reduced to a partial vacuum of approximately negative 0.7 bar, and then is increased again to approximately positive 0.7 bar. This pulse is applied three times, as shown in FIG. 2, or such greater or lesser number of times as may be necessary to achieve substantially complete removal of air entrapped in the dialyzer. Each such pulse takes approximately eight minutes in a preferred embodiment.

The steam pressure is then increased at a relatively high level for a dwell time of approximately 15 minutes. The dwell pressure is about 1.1 bar in the preferred embodiment. During this phase, the steam is at a temperature sufficient to provide a 12 Fo level of sterilization. Other sterilization levels may be used for various applications, including sterilization levels of about 10 or 14 Fo. In a preferred embodiment, a sterilization level of 12 Fo is obtainable under a dwell time of 15 minutes if the steam is heated to approximately 121°.

The final portion of the vacuum drying process is to provide a series of vacuum pulses to remove the steam and any condensate from the dialyzer. Each vacuum pulse begins with the application of a negative pressure, to approximately negative 0.9 bar in a preferred embodiment. The pressure is then increased, by adding air or another inert gas slowly for about 2 minutes, and quicker for a period of less than a minute, to bring the pressure up to about negative 0.3 bar where it is maintained for about a minute. This cycle is repeated for a number of times until the dialyzer is essentially dry. In a preferred embodiment this typically requires about nine such cycles or "pulses." As used in defining pressure levels in the claims herein, the word "approximately" means within 10 percent.

As described above, the application of a vacuum to the dialyzer after the steam autoclaving serves to remove residual gaseous and liquid water. If the vacuum were applied continuously, however, differential cooling, and consequent differential shrinkage, would result between the dialyzer housing and the potting material. This is because the potting material reserves the absorbent microfibers which are subjected to evaporative cooling long after the dialyzer housing has become dry.

Interspersing the vacuum with pulses of a lesser vacuum achieved by introducing air or some other gas reduces this differential cooling.

There are at least two reasons for this. One is that the air or other gas conductively cools the dialyzer housing by passing it on the way in and out of the chamber. The dialyzer housing cooling thus tends to "catch up" with the potting material cooling. The other reason is that the reduced vacuum during the period when the air or other gas is introduced lessens the evaporative cooling from the microfibers which are potted by the potting material. This is because moisture evaporates into a low vacuum quicker than into a high vacuum.

Although this process is described in the context of a dialyzer it will be appreciated that it is equally applicable to any other medical device or other device in which there are materials having differing coefficients of thermal expansion and differing absorptive properties, on which pathogens are destroyed by steam. Such devices may include, for example, blood filters, aphaeresis devices, and other extracorporeal devices such as line sets.

What is claimed is:

1. A method for destroying pathogens in a device including a first material joined to a second material and for preventing delamination of the first and second materials, the first material having a first coefficient of thermal expansion and the second material having a second coefficient of thermal expansion different from the first coefficient, the method comprising:
    (a) applying heated steam to the device at a first pressure in a chamber to destroy pathogens;
    (b) removing said steam and any condensate from said chamber by applying a second pressure to the device, wherein said second pressure is lower than said first pressure;
    (c) interspersing said second pressure with at least one pulse of a third pressure that is between said first pressure and said second pressure, said pulse being accomplished by adding a gas to the chamber at a first flow rate for about two minutes, and then adding the gas at a second flow rate, the second flow rate being greater than the first flow rate; and
    repeating steps (b) and (c) at least two more times, wherein the at least three pulses of the third pressure control a temperature differential between the first and second materials and prevent delamination of the first material from the second material.

2. The method of claim 1, wherein said gas is air.

3. The method of claim 1, wherein said first pressure is greater than atmosphere.

4. The method of claim 3, wherein said second pressure is less than atmosphere.

5. The method of claim 4, wherein said first pressure is over 1.0 bar.

6. The method of claim 4, wherein said first pressure is approximately 1.0 bar.

7. The method of claim 5, wherein said second pressure is negative 0.9 bar or less.

8. The method of claim 5, wherein said second pressure is approximately negative 0.9 bar.

9. The method of claim 5, wherein said third pressure is approximately negative 0.3 bar.

10. The method of claim 1, wherein the number of said pulses is sufficient to produce a desired level of dryness in the device.

11. The method of claim 1, wherein the first pressure is applied for a first period of time, and the first pressure and said first period of time are sufficient to produce a desired level of sterility in the device.

12. The method of claim 1, wherein said pulses are at least nine in number.

13. The method of claim 1, wherein said device is a medical device.

14. The method of claim 1, wherein said device is a dialyzer.

15. The method of claim 14, wherein said dialyzer includes absorptive microfibers.

16. The method of claim 1, further comprising, before said applying step, a step of pulsing steam into the chamber to remove entrapped air.

17. The method of claim 16, wherein said pulsing step includes introducing pressurized steam to the chamber and removing said steam.

18. The method of claim 17, wherein said steam introduced to the chamber is at greater than atmospheric pressure, and said steam is removed by reducing the chamber pressure to less than atmosphere.

19. The method of claim 18, wherein at least three pulses of pressurized steam are introduced to the chamber.

20. A method of drying a device including a first material joined to a second material and of preventing delamination of the first and second materials, the first material having a first coefficient of thermal expansion and the second material having a second coefficient of thermal expansion different from the first coefficient, the method comprising:
   (a) positioning the device in a chamber;
   (b) applying a pressure less than atmosphere to the chamber in at least three pulses, each pulse including reducing the chamber pressure to a first pressure less than atmosphere and then increasing the chamber pressure to a second pressure less than atmosphere by adding a gas to the chamber at a first flow rate for about two minutes, and then adding the gas at a second flow rate, the second flow rate being greater than the first flow rate,
   wherein said at least three pulses control a temperature differential between the first and second materials and prevent delamination of the first material from the second material.

21. A method of drying a dialyzer that has been subjected to steam sterilization so as to lessen differential shrinkage caused by differential cooling rates in the dialyzer between a housing and a potting material joined to the housing to help prevent delamination of the housing and potting materials, the method comprising:
   (a) placing the dialyzer in a chamber;
   (b) applying a partial vacuum to the dialyzer to allow evaporation of water into the vacuum to thereby evaporatively cool surfaces from which said water evaporates;
   (c) increasing the pressure in said chamber to reduce evaporation of said water and to thereby reduce evaporative cooling from said surfaces by adding a gas to said chamber at a first flow rate for about two minutes, and then adding the gas at a second flow rate, the second flow rate being greater than the first flow rate; and
   (d) repeating steps (b) and (c) at least two more times, wherein increasing the pressure at least three times controls a temperature differential between the housing and the potting material and prevents delamination of the housing from the potting material.

22. A dialyzer dried in accordance with the process of claim 21.

23. A method of sterilizing a device including a first material joined to a second material and of preventing delamination of the first and second materials of the device, the first material having a first coefficient of thermal expansion and the second material having a second coefficient of thermal expansion different from the first coefficient, the method comprising:
   (a) inserting the device into an autoclave;
   (b) introducing steam into the autoclave to sterilize the device;
   (c) applying vacuum pressure to the autoclave until a pressure within the autoclave reaches approximately negative 0.9 bar;
   (d) adding a gas to the autoclave at a first flow rate for about two minutes, and then adding the gas at a second flow rate, the second flow rate being greater than the first flow rate, the pressure within the autoclave reaching approximately negative 0.3 bar after adding the gas;
   (e) after adding the gas, maintaining the pressure within the autoclave at approximately negative 0.3 bar for about one minute; and
   (f) repeating steps (c) through (e) multiple times.

24. The method of claim 23, wherein the method comprises performing steps (c) through (e) about nine times.

* * * * *

UNITED STATES PATENT AND TRADEMARK OFFICE
CERTIFICATE OF CORRECTION

| | | |
|---|---|---|
| PATENT NO. | : 7,125,516 B2 | Page 1 of 1 |
| APPLICATION NO. | : 10/421602 | |
| DATED | : October 24, 2006 | |
| INVENTOR(S) | : Marion Andersen et al. | |

It is certified that error appears in the above-identified patent and that said Letters Patent is hereby corrected as shown below:

Title page, Other Publications item 56, col. 2, line 22, delete "lab8ahtm" and replace with --lab8a.htm--.

Signed and Sealed this

Eighteenth Day of September, 2007

JON W. DUDAS
*Director of the United States Patent and Trademark Office*